US008012694B2

(12) United States Patent
Zahradnik et al.

(10) Patent No.: US 8,012,694 B2
(45) Date of Patent: Sep. 6, 2011

(54) ASSAY FOR THE DETECTION OF PHOSPHORYLATED PTH

(75) Inventors: Richard J. Zahradnik, Dana Point, CA (US); Jeffrey R. Lavigne, San Juan Capistrano, CA (US)

(73) Assignee: Immutopics, Inc., San Clemente, CA (US)

( * ) Notice: Subject to any disclaimer, the term of this patent is extended or adjusted under 35 U.S.C. 154(b) by 1333 days.

(21) Appl. No.: 11/521,007

(22) Filed: Sep. 14, 2006

(65) Prior Publication Data

US 2010/0261199 A1 Oct. 14, 2010

(51) Int. Cl.
*A61K 38/29* (2006.01)
*C07K 16/06* (2006.01)
*C07K 16/26* (2006.01)
*G01N 33/53* (2006.01)
*G01N 33/566* (2006.01)
*G01N 33/577* (2006.01)

(52) U.S. Cl. ....... 435/7.1; 435/7.93; 436/501; 514/11.8; 530/327; 530/389.2

(58) Field of Classification Search .................. None
See application file for complete search history.

(56) References Cited

U.S. PATENT DOCUMENTS

| 4,341,755 | A | | 7/1982 | Lindall et al. | |
|---|---|---|---|---|---|
| 5,807,823 | A | * | 9/1998 | Krstenansky et al. | ....... 514/11.8 |
| 6,030,790 | A | | 2/2000 | Adermann et al. | |
| 6,107,049 | A | | 8/2000 | Allard et al. | |
| 6,743,590 | B1 | * | 6/2004 | Cantor et al. | ................... 435/7.1 |
| 6,838,264 | B2 | * | 1/2005 | Zahradnik et al. | ......... 435/70.21 |
| 7,226,749 | B2 | * | 6/2007 | Zahradnik et al. | ............. 435/7.1 |
| 7,288,253 | B2 | * | 10/2007 | Roskos et al. | ............. 424/158.1 |
| 7,318,925 | B2 | * | 1/2008 | Roskos et al. | ............. 424/145.1 |
| 7,541,140 | B2 | * | 6/2009 | Cantor | .............................. 435/4 |
| 7,670,805 | B2 | * | 3/2010 | Zahradnik et al. | ......... 435/70.21 |
| 7,820,393 | B2 | * | 10/2010 | Cantor et al. | ................... 435/7.1 |

FOREIGN PATENT DOCUMENTS

| DE | 4434551 | 4/1996 |
|---|---|---|
| WO | WO 00/42437 | 7/2000 |
| WO | WO 02/08271 | 1/2002 |
| WO | WO 0214504 | 2/2002 |
| WO | 2005/018413 | 3/2005 |
| WO | 2006/039258 | 4/2006 |

OTHER PUBLICATIONS

Kuby et al, Immunology, second edition, pp. 85-96, 1994.*
Abaza et al, J of Protein Chemistry 11(5): 433-444, 1992.*
Kuby et al., Immunology, Second edition, pp. 86-96, 1994.
Coleman et al., "Effects of amino acid sequence changes on antibody-antigen interactions"; A Structural View of Immune Recognition by Antibodies, pp. 33-36, 1994.
Abaza et al., "Effects of Amino Acid Substitutions Outside an Antigenic Site on Protein Binding . . . " Journal of Protein Chemistry; 11(5): 433-444, 1992.
Harlow et al., Antibodies, a Laboratory Manual, 1988, Cold Spring Harbor Laboratory publication, Cold Spring Harbor, NY, pp. 92-94, and pp. 323-358.
Ratcliffe et al., "Production and characterisation of monoclonal antibodies to parathyroid . . . "; Journal Immunological Methods, 127(1): 109-16, Feb. 1990.
Ikeda et al., "Development of a sensitive two-site immunoradiometric assay for parathyroid . . . "; Journal of Clinical Endocrinology & Metabolism; 79(6): 1322-27, 1994.
Heinrich et al., "Gene encoding parathyroid hormone", Journal of Biological Chemistry; 259(5): 3320-3329, Mar. 1984.
Markus et al.; "A novel immunoradiometric assay detects full-length human PTH . . . "; Journal of Clinical Endocrinology & Metabolism; vol. 84(11); 4287-4290; 1999.
Nussbaum et al.; "Highly sensitive two-site immunoradiometric assay of parathyrin . . . "; reprinted from Clinical Chemistry, 1364-1367; Aug. 1987.
D'Amour, Pierre et al; Amino-Terminal Form of Parathyroid Hormone (PTH) with Immunologic Similarities to hPTH (1-84) is Overproduced in Primary and Secondary Hyperparathyroidism; Clinical Chemistry; 2003; pp. 2037-2044; 49:12.
Boudou, Philippe, et al; Unexpected Serum Parathyroid Hormone Profiles in Some Patients with Primary Hyperparathyroidism; Clinical Chemistry; 2006; pp. 757-760; 52:4.
Rakel, Agnes, et al; Overproduction of an amino-terminal form of PTH distinct from human PTH(1-84) in a case of severe primary hyperparathyroidism: influence of medical treatment and surgery; Clinical Endocrinology; 2005; pp. 721-727; 62.
Tanaka, M. et al; Normalization of reversed bio-intact-PTH(1-84) / intact-PTH ratio after parathyroidectomy in a patient with severe secondary hyperparathyroidism; Clinical Nephrology; 2005; pp. 69-72; vol. 64.
Arakawa, Toshio, et al; Overproduction and secretion of a novel amino-terminal form of parathyroid hormone from a severe type of parathyroid hyperplasia in uremia; American Society of Nephrology; 2006; pp. 525-531; vol. 1.
Rubin, M.R., et al; A molecular form of PTH distinct from PTH(1-84) is produced in parathyroid carcinoma; Journal of Bone and Mineral Research 2004 Abstracts; 2004; p. S327; vol. 1.
Declaration of Interference, between U.S. Appl. No. 10/641,780 and U.S. Patent No. 6,838,264, Patent Interference No. 105,575 (MPT), mailed on Aug. 30, 2007.

(Continued)

*Primary Examiner* — Phuong Huynh
(74) *Attorney, Agent, or Firm* — Stetina Brunda Garred & Brucker

(57) ABSTRACT

Antibodies for a variant of intact parathyroid hormone (PTH) or its fragments which have at position 17 the amino acid serine which is phosphorylated [p(17) PTH] and methods of producing the same. The invention further includes various immunoassay methods which use the described antibody alone or in combination with other antibodies to determine the circulating levels of p(17) intact PTH (1-84) or fragments thereof in biological fluids. Such antibodies and immunoassays can be used in conjunction with other antibodies to detect all biologically active forms of hPTH present in biological fluids.

5 Claims, 2 Drawing Sheets

OTHER PUBLICATIONS

Mizumura, Y, et al; The reversed ratio of 1-84 PTH (whole PTH) / intact PTH in a patient on hemodialysis associated with primary hyperparathyroidism; Clinical Nephrology vol. 69-No. 4/2008, 310-312.

Komaba, Hirotaka, Reversed whole PTH/intact PTH ratio as an indicator of marked parathyroid enlargement; five case studies and a literature review, Nephrology Dialysis Transplantation NDT Plus; 2008, 1, Suppl 3, iii54-iii58.

Komava, Hirotaka, Spontaneous remission of severe hyperparathyroidism with normalization of the reversed whole PTH/intact PTH ratio in a maemodialysis patient, Nephrology Dialysis Transplantation NDT, 2008, 23, 1760-1762.

Rubin, Mishaela R., An N-Terminal Molecular Form of Parathyroid Hormone (PTH) Distinct from hPTH(1-84) Is Overproduced in Parathyroid Carcinoma, Clinical Chemistry, 2007, 53:8, 1470-1476.

Huse, Klaus, Hans-Joachim Bohme, Gerard H. Scholz; Purification of antibodies by affinity chromatography; J. Biochem. Biphys. Methods 51 (2002) 217-231.

* cited by examiner

Fig. 1 (SEQ ID NO. 1)

```
  1               5                   10                  15                  20
Ser Val Ser Glu Ile Gln Leu Met His Asn Leu Gly Lys His Asn Ser Met Glu     Arg
Val Glu Trp Leu Arg Lys Lys Leu Gln Asp Val His Asn Phe Ala Leu Gly Ala     Pro
Leu Ala Pro Arg Asp Ala Gly Ser Gln Asp Pro Arg Lys Lys Asp Asn Val Leu     Val
Glu Ser His Glu Lys Ser Leu Gly Glu Ala Asp Lys Ala Asp Asn Val Leu Thr     Lys
Ala Lys Ser Gln
```

Fig. 2A (SEQ ID NO. 2)

```
  1               5                   10
Lys His Leu Asn Ser Met Glu Arg Val Glu
```

Fig. 2B (SEQ ID NO. 3)

```
  1               5                   10
Cys Lys His Leu Asn Ser Met Glu Arg Val Glu
```

Fig. 3 (SEQ ID NO. 4)

```
  1               5                   10                  15
Ser Val Ser Glu Ile Gln Leu Met His Asn Leu Gly Lys His Leu
Asn Ser Met Glu Arg Val Glu Trp Leu Arg Lys Lys Leu Gln Asp
Val His Asn Phe
```

Fig. 4 (SEQ ID NO. 5)

```
1                   5
Val Leu Thr Lys Ala Lys Ser Gln
```

Fig. 5 (SEQ ID NO. 6)

```
1               5               10              15
Ala Pro Leu Ala Pro Arg Asp Ala Gly Ser Gln Arg Pro Arg Lys
Lys Glu Asp Asn Val Leu Val Val Ser His Glu Lys Ser Leu Gly
Glu Ala Asp Lys Ala Asp Val Ala Ala Asn Thr Lys Ala          
Gln
```

Fig. 6 (SEQ ID NO. 7)

```
1               5               10              15
Arg Asp Ala Gly Ser Gln Arg Pro Arg Lys Lys Glu Asp Asn Val
Leu Val Val Gly Ser His Glu Lys Ser Leu Gly
```

Fig. 7 (SEQ ID NO. 8)

```
1
Ser Val Ser
```

ASSAY FOR THE DETECTION OF PHOSPHORYLATED PTH

CROSS-REFERENCE TO RELATED APPLICATIONS

Not Applicable

SEQUENCE REFERENCE ON COMPACT DISC

This application references and incorporates by reference two (2) identical compact discs filed herewith in compliance with 1.52(e), created in September 2006, including amino acid SEQ ID NOS. 1-7. The compact discs each contain a single 3,029 byte file named "IMUNE010A.txt" created on Sep. 13, 2006.

STATEMENT RE: FEDERALLY SPONSORED RESEARCH/DEVELOPMENT

Not Applicable

BACKGROUND

1. Field of the Invention

The present invention relates to high affinity and specific antibodies for a variant of human intact parathyroid hormone [hPTH (1-84)] (SEQ ID NO. 1) or its fragments which have at position 17 the amino acid serine which is phosphorylated [p(17) hPTH] and a method for preparing such antibodies. The invention further includes various immunoassay methods which use the described antibody alone or in combination with other antibodies to determine the circulating levels of intact p(17) hPTH (1-84) (SEQ ID NO. 1) or fragments thereof in biological fluids.

2. Background of the Invention

Parathyroid hormone (PTH) and its importance in regulating the concentration of calcium ions in the blood is well known. In this regard, PTH is created by the parathyroid glands and, in combination with other factors, functions to regulate the blood calcium ion levels such that they are maintained in a steady concentration in cells and the surrounding fluids. Essentially, PTH functions to release stored calcium in the body when serum calcium levels decrease. On the other hand, such secretion is suppressed to the extent serum calcium concentration increases.

In its complete bioactive form, hPTH comprises a unique peptide comprised of 84 amino acids (SEQ ID NO. 1). Given its significance in calcium metabolism, accurately measuring PTH has and continues to be of substantial clinical significance. As is well documented, serum PTH levels serve as an important parameter for patients having diseases such as hypercalcemia, primary hyperparathyroidism, and osteoporosis, among many others. PTH likewise becomes of substantial clinical importance in patients afflicted with chronic renal failure who, because of an excess in PTH production, can develop renal osteodystrophy.

Notwithstanding its important role in metabolism and clinical significance, substantial difficulties have and continue to exist with regard to determining circulating biologically active PTH levels. First of all, it is well known that PTH is normally present at extremely low levels, which are normally between 5 pg/mL to 45 pg/mL. Furthermore, it is well known that the PTH peptide is also present as a variety of circulating PTH fragments, including amino-terminally truncated fragments which are not bioactive. Second generation PTH assays were known to measure many of these non-bioactive fragments as well as the bioactive PTH, thereby leading to results that showed a PTH level higher than the actual circulating bioactive PTH levels. Third generation assays were able to overcome this shortcoming by binding to the amino-terminal end of PTH, thereby giving a more accurate reading of the bioactive PTH levels in a patient.

However, D'Amour et al. describe an amino-terminal form of hPTH that can be separated from hPTH (1-84) by HPLC. *Amino-Terminal Form of Parathyroid Hormone (PTH) with Immunologic Similarities to hPTH (1-84) is Overproduced in Primary and Secondary Hyperparathyroidism*, Clin Chem 49:12, 2037-2044 (2003). The article further postulates that this variant may be hPTH that is phosphorylated at the serine residue in position 17. An important finding of this paper is that the percentage of this new form of hPTH to intact hPTH (1-84) varied by disease state. Specifically, the new form of hPTH was lowest in the non-diseased control group, was increased in the renal failure patients, and was the highest in patients having primary hyperparathyroidism. Accordingly, there is a need in the art for an assay that can efficiently and cost-effectively measure this new form of hPTH.

Third generation bioactive hPTH assays that only bind to the first few amino acids of the amino terminal recognize this new form of hPTH along with intact hPTH (1-84). However, second generation hPTH assays that recognize both intact hPTH (1-84) and amino-terminally truncated hPTH fragments such as hPTH (7-84) have diminished recognition to this new form of hPTH. Since the antibodies utilized in second generation assays usually bind in the region of amino acid 17 of hPTH, this diminished recognition to hPTH is further suggestive of a possible modification, such as phosphorylation, at this amino acid site.

These binding characteristics could explain a phenomenon described in a recent article by Boudou et al. *Unexpected Serum Parathyroid Hormone Profiles in Some Patients with Primary Hyperparathyroidism*, Clin Chem 52:4, 757-760 (2006). Typically, second generation hPTH assays yield patient results that are higher than third generation hPTH results because the second generation assays detect amino-terminally truncated hPTH fragments in addition to intact hPTH (1-84). The article by Boudou et al. describes seven patients in which this ratio is reversed, that is the third generation assays produce a higher patient result than the second generation assays. This is potentially due to increased amounts of p(17) hPTH which was undetected by the second generation PTH assays. The seven patients presented clinically with severe primary hyperparathyroidism and the authors further speculate that this unexpected profile may be predictive of malignancy. As this study used only indirect evidence, an assay that can directly measure p(17) hPTH may prove extremely valuable for assessing hyperfunctional parathyroid gland activity.

BRIEF SUMMARY

The present invention is directed to certain novel antibodies, methods for producing such antibodies, and methods utilizing such antibodies in order to determine the amount of a specific PTH or PTH fragment in a sample fluid, such as serum, plasma, or cell culture media. In particular, such antibodies are specific for PTH or PTH fragments wherein the serine amino acid located at position 17 of the PTH molecule is phosphorylated [p(17) PTH].

One embodiment of the invention is a substantially pure antibody or antibody fragment which is specific for a parathyroid hormone having a phosphorylated serine amino acid at position 17. The antibody or antibody fragment may be specific for a parathyroid hormone epitope consisting of amino acids 13-22, i.e., Lys-His-Leu-Asn-Ser-Met-Glu-Arg-Val-Glu (SEQ ID NO. 2).

Another embodiment of the present invention contemplates a method for producing antibodies useful in the determination of p(17) PTH levels in a biological sample. The first step of the method is administering a first peptide antigen to a host animal to induce an immunological reaction in the host animal. The first peptide antigen has an amino acid sequence substantially similar to a portion of PTH including at least the amino acid serine present at the seventeenth residue in PTH wherein the serine is phosphorylated. Next, the antibody titer produced by the administration of the first peptide antigen to the host animal is monitored. When appropriate, the antisera produced in said host animal is extracted. The extracted antiserum is then subjected to affinity chromatography. In particular, the antisera may be run over an affinity column having a second peptide antigen. The second peptide antigen is a bioactive form of p(17) PTH, enabling the recovery of antibodies from the antisera that have affinity for the bioactive form of p(17) PTH upon elution. The antibodies recovered from the elution phase are then subjected again to affinity chromatography. This time, the antibodies may be run over an affinity column containing a third peptide antigen. The third peptide antigen is a non-phosphorylated form of bioactive PTH. By isolating the antibodies recovered from the flow-thru of the column, one is able to recover at least one antibody that has affinity for the phosphorylated form of bioactive PTH but does not have affinity for the non-phosphorylated form to ensure that only the phosphorylated form of PTH is measured by the recovered antibodies.

The first peptide antigen may be coupled to a carrier protein, for example maleimide activated keyhole limpet hemocyanin (KLH). The first peptide antigen may be Cys-12 hPTH (13-22), i.e., the amino acid sequence Cys-Lys-His-Leu-Asn-Ser-Met-Glu-Arg-Val-Glu (SEQ ID NO. 3), wherein the cysteine amino acid is added to PTH (13-22) (SEQ ID NO. 2) to aid in coupling. Although not limited to the following, the second peptide antigen may be p(17) PTH (1-84) (SEQ ID NO. 1) or p(17) PTH (1-34) (SEQ ID NO. 4). Although not limited to the following, the third peptide antigen may PTH (1-34) (SEQ ID NO. 4) or PTH (1-84) (SEQ ID NO 1).

Yet another embodiment of the invention consists of methods for measuring an amount of p(17) PTH in a biological sample. One such method includes adding to the sample an antibody specific for p(17) PTH and a labeled bioactive p(17) PTH. The p(17) PTH in the sample and the labeled bioactive p(17) PTH compete for and bind with binding sites on the p(17) PTH antibody. The amount of labeled p(17) PTH bound to the antibody is measured in order to determine the amount of p(17) PTH in the sample. Since this is a competition immunoassay, the amount of bound labeled p(17) PTH is inversely proportional to the amount of p(17) PTH in the sample. The antibody may be specific for a parathyroid hormone epitope consisting of amino acids 13-22 (SEQ ID NO. 2). The antibody may be bound to a solid support or may be added in liquid form and potentially later precipitated. The labeled bioactive p(17) PTH may include a detectable moiety consisting of an enzyme, a fluorescent chemical, a radioisotope, a chemiluminescent chemical, or a colorimetric agent. Although not limited to the following, the labeled bioactive p(17) PTH may be p(17) PTH (1-34) (SEQ ID NO. 4) or p(17) PTH (1-84) (SEQ ID NO. 1).

A different method for measuring the amount of p(17) PTH in the sample includes adding to the sample a first antibody specific for p(17) PTH wherein the first antibody binds with at least the phosphorylated seventeenth amino acid of PTH. A second antibody that is specific to a portion of PTH other than the portion with which said first antibody binds is also added to the sample. One of the two antibodies is labeled with a detectable moiety. The two antibodies are allowed to bind with the p(17) PTH in the sample and thereby form a labeled complex consisting of p(17) PTH, the first antibody, and the second antibody. The amount of labeled complex is then measured to determine the amount of p(17) PTH in the sample. The second antibody may be bound to a solid support or added to the sample in liquid form. The method may further include precipitating the labeled complex. The first or the second antibody may include a detectable moiety consisting of an enzyme, a fluorescent chemical, a radioisotope, a chemiluminescent chemical, or a colorimetric agent. The second antibody may be added either simultaneously or sequentially to the first antibody. The first antibody may be specific for a parathyroid hormone epitope consisting of amino acids 13-22 (SEQ ID NO. 2). Although not limited to the following, the second antibody may be specific for parathyroid hormone epitopes consisting of amino acids 77-84 (SEQ ID NO. 5), amino acids 39-84 (SEQ ID NO. 6), amino acids 44-68 (SEQ ID NO. 7), or amino acids 1-3 (SEQ ID NO. 8).

BRIEF DESCRIPTION OF THE DRAWINGS

These as well as other features of the present invention will become more apparent upon reference to the drawings.

FIG. 1 is an amino acid listing of the hPTH (1-84) protein (SEQ ID NO. 1);

FIG. 2A is an amino acid listing of the hPTH (13-22) peptide (SEQ ID NO. 2);

FIG. 2B is an amino acid listing of the Cys-12 hPTH (13-22) peptide (SEQ ID NO. 3);

FIG. 3 is an amino acid listing of the hPTH (1-34) peptide (SEQ ID NO. 4);

FIG. 4 is an amino acid listing of the hPTH (77-84) peptide (SEQ ID NO. 5);

FIG. 5 is an amino acid listing of the hPTH (39-84) peptide (SEQ ID NO. 6);

FIG. 6 is an amino acid listing of the hPTH (44-68) peptide (SEQ ID NO. 7); and

FIG. 7 is an amino acid listing of the hPTH (1-3) peptide (SEQ ID NO. 8).

DETAILED DESCRIPTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

Production of p(17) hPTH Antibodies

An eleven amino acid peptide consisting of the thirteenth through twenty-second amino acids of human parathyroid hormone with a cysteine amino acid at position twelve and wherein the seventeenth amino acid is phosphorylated [Cys-12 p(17) hPTH (13-22)] (SEQ ID NO. 3) was synthesized by conventional means known within the art. The specific amino acid sequence of the peptide is Cys-Lys-His-Leu-Asn-Ser-Met-Glu-Arg-Val-Glu (SEQ ID NO. 3) and, as mentioned previously, the serine amino acid located at position 17 is phosphorylated. The peptide was then conjugated to maleimide activated keyhole limpet hemocyanin (KLH). Goats were immunized with the conjugated phosphorylated peptide by conventional means known within the art. After several months, antisera were drawn from the immunized goats. An eleven amino acid peptide was used to immunize the goats, rather than a longer peptide, in order to minimize the creation of antibodies non-specific for the phosphorylated seventeenth amino acid region of hPTH. A p(17) hPTH (1-34) peptide (SEQ ID NO. 4) was synthesized by conventional means and covalently linked to a CNBr-activated Sepharose 4B affinity column. Although a p(17) hPTH (1-34) peptide (SEQ ID NO. 4) was used, it is contemplated that a p(17) hPTH (1-84) peptide (SEQ ID NO. 1) could also be used, since both molecules are biologically active. A biologically active peptide is linked to the affinity column rather than the Cys-12 p(17) hPTH (13-22) (SEQ ID NO. 3) so as to select antibodies that bind to the conformationally correct structure of the circulating p(17) hPTH.

The antisera were then passed over the prepared affinity columns, unbound proteins were subsequently washed from the column, and bound antibodies were eluted from the column, all of which were effectuated using conventional means well known within the art. A second set of affinity columns was prepared by covalently linking a non-phosphorylated hPTH (1-34) peptide (SEQ ID NO. 4) to CNBr-activated Sepharose 4B. Again, although an hPTH (1-34) peptide (SEQ ID NO. 4) was used, it is contemplated that an hPTH (1-84) peptide (SEQ ID NO. 1) could be used since both are biologically active forms of hPTH. The antibodies recovered from the elution step of the p(17) hPTH columns were then passed over the hPTH (1-34) columns to remove that portion of the p(17) hPTH antibodies that recognize and bind to the non-phosphorylated forms of hPTH. This step is essential to ensure that the specificity of the final antibody preparation is exclusive for the phosphorylated version of hPTH. The result of these steps is a purified p(17) hPTH antibody.

Immunoassay Methods for Detecting and Quantitating Levels of Circulating p(17) hPTH (1-84) and p(17) hPTH Fragments 1. Competitive Inhibition Assay A limited amount of p(17) hPTH antibody is combined with p(17) hPTH (1-34) peptide (SEQ ID NO. 4) or p(17) hPTH (1-84) peptide (SEQ ID NO. 1), which is labeled with a detectable moiety, along with the sample to be tested for p(17) hPTH. The labeled p(17) hPTH and the unlabeled p(17) hPTH present in the sample compete for the limited number of binding sites on the antibody. After an incubation period, unbound p(17) hPTH, both labeled and unlabeled, are removed from the reaction mixture and the amount of labeled p(17) hPTH bound to the antibody is measured. The amount of labeled p(17) hPTH measured is inversely proportional to the concentration of p(17) hPTH in the sample. Standards are run at the same time to quantify the amount of p(17) hPTH present in the sample.

The p(17) hPTH antibody may be immobilized to a solid phase prior to the assay or used as a liquid to be immobilized or precipitated after the incubation. This assay detects intact p(17) hPTH (1-84) (SEQ ID NO. 1) as well as all fragments of hPTH which include a phosphorylated serine at position seventeen.

2. Two-Site "Sandwich" Immunometric Assays

These assays include two different antibodies to hPTH, one of which is the p(17) hPTH antibody and the other directed to a portion of the hPTH molecule that is dissimilar to the portion of which the p(17) hPTH antibody is directed. Either one of the antibodies could be labeled with a detectable moiety. The other antibody could be immobilized to a solid phase prior to assay or later immobilized by reacting with a solid phase specific for that antibody.

This two-site "sandwich" immunometric assay is performed by reacting a standard containing a known amount of p(17) hPTH with the two antibodies, either sequentially or simultaneously, followed by an incubation period. The desired sample is also combined with the two antibodies and incubated. The two antibodies bind to p(17) hPTH present in the standard or sample and form a labeled antibody-p(17) hPTH complex. Unlabeled antibody is then washed from the final solid phase-bound labeled complex. This bound sandwich complex is then measured to determine the level of p(17) hPTH present in the sample. Unlike in the competitive assay described above, in this case the results are directly proportional to the concentration of p(17) hPTH present in the sample.

A number of schemes utilizing the two-site immunometric assay are possible. Antibody combinations used may be, but are not limited to: an antibody specific for hPTH (77-84) (SEQ ID NO. 5) in combination with a p(17) hPTH antibody, an antibody specific for hPTH (39-84) (SEQ ID NO. 6) in combination with a p(17) hPTH antibody, an antibody specific for hPTH (44-68) (SEQ ID NO. 7) in combination with a p(17) hPTH antibody, or an antibody specific for hPTH (1-3) (SEQ ID NO. 8) in combination with a p(17) hPTH antibody. All of the previous schemes would measure p(17) hPTH (1-84) (SEQ ID NO. 1) as well as various but different hPTH fragments that include a phosphorylated serine at position seventeen. The last scheme would measure all of the biologically active forms of p(17) hPTH, that is, all of the hPTH forms that bind to and activate the hPTH receptor.

Immunoassays utilizing the anti-hPTH (77-84) and anti-hPTH (39-84) antibodies have been produced wherein the p(17) hPTH antibody was labeled with peroxidase and the other antibody was biotinylated. These ELISA assays were carried out in streptavidin-coated microtitre plates and utilized p(17) hPTH (1-84) (SEQ ID NO. 1) as standards. 50 µL of each standard plus 50 µL of the combined antibodies were added to the wells of the microtitre plate. The plates were then incubated on a horizontal rotator for three hours and then washed. 100 µL of TMB was added and incubated on the horizontal rotator for an additional 30 minutes to allow for reaction with peroxidase and adequate color development. The reaction was stopped by adding 50 µL of HCl. The plates were then read in a spectrophotometer at 450 nm. Both ELISA assays were sensitive to a lower limit of 1 to 4 pg/mL.

The above description is given by way of example, and not limitation. Given the above disclosure, one skilled in the art could devise variations that are within the scope and spirit of the invention disclosed herein. For example, although the cited experiments were directed toward human PTH, the serine amino acid is conserved at the seventeenth position in all mammalian species and as such the methods of the present invention could be used to produce p(17) PTH antibodies for other mammalian species and immunoassays specific for p(17) PTH of other mammalian species by modifying the immunization peptide to account for the different PTH sequence of the desired species. An additional use of the p(17) hPTH antibody would be to include it in assays for the measurement of hPTH that use at least one antibody directed toward an epitope of the hPTH molecule that includes serine at position seventeen. This would allow the assay to detect both the phosphorylated and non-phosphorylated forms of the hPTH molecule or fragment and would preclude the errors found in the present second generation hPTH assays. In addition, immunoassays designed to detect all biologically active forms of hPTH would need to include an antibody to hPTH (1-3) (SEQ ID NO. 8) plus a combination of antibodies to detect both the phosphorylated and non-phosphorylated hPTH that include the amino acid sequence 13-22 (SEQ ID NO. 2) as both hPTH segments are needed to insure not only receptor binding but also activation, and both hPTH and p(17) hPTH have been shown to be biologically active. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. An isolated antibody or an antigen binding fragment thereof that specifically binds to human parathyroid hormone (SEQ ID NO. 1) having a phosphorylated serine amino acid at position 17.

2. The antibody or antibody fragment of claim 1 wherein the antibody or antigen binding fragment thereof specifically binds to human parathyroid hormone at an epitope consisting of amino acids 13-22 (SEQ ID NO. 2).

3. A method for producing antibodies useful in the determination of PTH levels in a biological sample, wherein the PTH has a phosphorylated serine amino acid at position 17 the method comprising the steps:

a. administering a first peptide antigen to a host animal to induce antibody production against said first peptide antigen in the host animal wherein said first peptide antigen comprises amino acids 13-22 (SEQ ID NO. 2) of human PTH (SEQ ID NO. 1), wherein the amino acid serine present at the seventeenth residue in said PTH and wherein said serine is phosphorylated;

b. monitoring antibody titer produced by the administration of said first peptide antigen to the host animal;

c. extracting antisera produced in said host animal;

d. subjecting the antisera extracted in step c) to affinity chromatography utilizing a second peptide antigen, wherein said second peptide antigen is a bioactive form of PTH selected from the group consisting of PTH (1-34) (SEQ ID NO. 4) and PTH (1-84) (SEQ ID NO. 1) wherein the bioactive form of PTH has a phosphorylated serine amino acid at position 17, to recover the antibodies from said antisera that have affinity for said second peptide antigen; and e. subjecting said antibodies recovered in step d) to affinity chromatography utilizing a third peptide antigen, wherein said third peptide antigen is a non-phosphorylated form of bioactive PTH selected from the group consisting of PTH (1-34) (SEQ ID NO. 4) and PTH (1-84) (SEQ ID NO. 1), to recover at least one antibody that does not have affinity for said third peptide antigen.

4. The method of claim 3 wherein said first peptide antigen in step a) is coupled to a carrier protein.

5. An isolated antibody produced by the method of claim 3.

* * * * *

```
                          SEQUENCE LISTING

<160> NUMBER OF SEQ ID NOS: 8

<210> SEQ ID NO 1
<211> LENGTH: 84
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 2
<211> LENGTH: 10
<212> TYPE: PRT
<213> ORGANISM: Artificial
<220> FEATURE:
<223> OTHER INFORMATION: Sythensized by conventional means.

<400> SEQUENCE: 2

Lys His Leu Asn Ser Met Glu Arg Val Glu
1               5                   10

<210> SEQ ID NO 3
<211> LENGTH: 11
<212> TYPE: PRT
<213> ORGANISM: Artificial
<220> FEATURE:
<223> OTHER INFORMATION: Synthesized by conventional means.

<400> SEQUENCE: 3

Cys Lys His Leu Asn Ser Met Glu Arg Val Glu
1               5                   10

<210> SEQ ID NO 4
<211> LENGTH: 34
<212> TYPE: PRT
<213> ORGANISM: Artificial
<220> FEATURE:
<223> OTHER INFORMATION: Synthesized by conventional means.

<400> SEQUENCE: 4

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe
```

-continued

```
<210> SEQ ID NO 5
<211> LENGTH: 8
<212> TYPE: PRT
<213> ORGANISM: Artificial
<220> FEATURE:
<223> OTHER INFORMATION: Synthesized by conventional means.

<400> SEQUENCE: 5

Val Leu Thr Lys Ala Lys Ser Gln
1               5

<210> SEQ ID NO 6
<211> LENGTH: 46
<212> TYPE: PRT
<213> ORGANISM: Artificial
<220> FEATURE:
<223> OTHER INFORMATION: Synthesized by conventional means,

<400> SEQUENCE: 6

Ala Pro Leu Ala Pro Arg Asp Ala Gly Ser Gln Arg Pro Arg Lys Lys
1               5                   10                  15

Glu Asp Asn Val Leu Val Glu Ser His Glu Lys Ser Leu Gly Glu Ala
            20                  25                  30

Asp Lys Ala Asp Val Asn Val Leu Thr Lys Ala Lys Ser Gln
        35                  40                  45

<210> SEQ ID NO 7
<211> LENGTH: 25
<212> TYPE: PRT
<213> ORGANISM: Artificial
<220> FEATURE:
<223> OTHER INFORMATION: Synthesized by conventional means.

<400> SEQUENCE: 7

Arg Asp Ala Gly Ser Gln Arg Pro Arg Lys Lys Glu Asp Asn Val Leu
1               5                   10                  15

Val Glu Ser His Glu Lys Ser Leu Gly
            20                  25

<210> SEQ ID NO 8
<211> LENGTH: 3
<212> TYPE: PRT
<213> ORGANISM: Artificial
<220> FEATURE:
<223> OTHER INFORMATION: Synthesized by conventional means.

<400> SEQUENCE: 8

Ser Val Ser
1
```